United States Patent
Amemiya et al.

(10) Patent No.: US 11,430,574 B2
(45) Date of Patent: Aug. 30, 2022

(54) MEDICAL IMAGE DIAGNOSIS SUPPORT DEVICE AND MAGNETIC RESONANCE IMAGING APPARATUS

(71) Applicant: Hitachi, Ltd., Tokyo (JP)

(72) Inventors: Tomoki Amemiya, Tokyo (JP); Yo Taniguchi, Tokyo (JP); Suguru Yokosawa, Tokyo (JP); Hisaaki Ochi, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 656 days.

(21) Appl. No.: 16/361,839

(22) Filed: Mar. 22, 2019

(65) Prior Publication Data
US 2019/0311806 A1    Oct. 10, 2019

(30) Foreign Application Priority Data

Apr. 5, 2018 (JP) .............................. JP2018-073257

(51) Int. Cl.
*G16H 50/20* (2018.01)
*G06T 7/00* (2017.01)
(Continued)

(52) U.S. Cl.
CPC .............. *G16H 50/20* (2018.01); *A61B 5/055* (2013.01); *A61B 5/7267* (2013.01);
(Continued)

(58) Field of Classification Search
CPC ........ G16H 50/20; G16H 30/40; G16H 50/70; G06T 7/0012; G06T 2207/20221; G06T 2207/20081; G06T 2207/10088; G06T 2207/30016; A61B 5/7267; A61B 5/055; G01R 33/5608; G01R 33/565;
(Continued)

(56) References Cited

U.S. PATENT DOCUMENTS

| 8,874,189 B2 | 10/2014 | Warntjes |
| 10,169,866 B2 | 1/2019 | Yokosawa et al. |
| 2011/0280456 A1* | 11/2011 | Sussman ............ G01R 33/5608 382/131 |

FOREIGN PATENT DOCUMENTS

JP    6250795 B2    12/2017

OTHER PUBLICATIONS

Conserve O Gram, Understanding Bit Depth, Aug. 2008, No. 22/1.*
(Continued)

*Primary Examiner* — Bo Joseph Peng
(74) *Attorney, Agent, or Firm* — Foley & Lardner LLP

(57) ABSTRACT

Two or more learning images generated for a first subject or a second subject and one or more correct answer images generated for the second subject or a third subject are received. In a case where pixel values of corresponding pixels of the two or more learning images are synthesized by using a synthesis parameter value, the parameter value at which the synthesized pixel values are close to a pixel value of a corresponding pixel of the correct answer image is obtained. An image generated for the first subject and having the same type as the two or more learning images is received as an examination target image. A synthesized image desired by a user is generated by synthesizing pixel values of corresponding pixels of the two or more examination target images by using the synthesis parameter value.

15 Claims, 11 Drawing Sheets

(51) Int. Cl.
*G16H 30/40* (2018.01)
*A61B 5/00* (2006.01)
*G01R 33/56* (2006.01)
*G01R 33/565* (2006.01)
*A61B 5/055* (2006.01)

(52) U.S. Cl.
CPC ....... *G01R 33/565* (2013.01); *G01R 33/5608* (2013.01); *G06T 7/0012* (2013.01); *G16H 30/40* (2018.01); *G06T 2207/10088* (2013.01); *G06T 2207/20081* (2013.01); *G06T 2207/20221* (2013.01)

(58) Field of Classification Search
CPC .............. G01R 33/5602; G01R 33/546; G01R 33/5607; G01R 33/50
See application file for complete search history.

(56) References Cited

OTHER PUBLICATIONS

Baxter, Procedure Manual for MRI of the Brain, Protocol 161003 A Phase 3 Randomized, Double-Blind, Placebo-Controlled Study of the Safety and Effectiveness of Immune Globulin Intravenous (Human), 10% Solution (IGIV, 10%) for the Treatment of Mild to Moderate Alzheimer's Disease (AD), Synarc Code: BAXT 2207, Versio.*
Joachim Graessner, Bandwidth in MRI, How-I-Do-It, MAGNETOM Flash, Feb. 2013.*
Hashido et al., Quantitative T1, T2, and T2 Mapping and Semi-Quantitative Neuromelanin-Sensitive Magnetic Resonance Imaging of the Human Midbrain, PLoS ONE 11 (10): e0165160. doi:10.1371/journal. pone.0165160, Oct. 21, 2016.*
Chartsias, et al., "Multimodal MR Synthesis via Modality-Invariant Latent Representation", IEEE Transactions on Medical Imaging, vol. 37, No. 3, Mar. 2018, pp. 803-814.
Office Action issued in corresponding Japanese Patent Application No. 2018-073257 dated Jan. 18, 2022 with English translation.

* cited by examiner

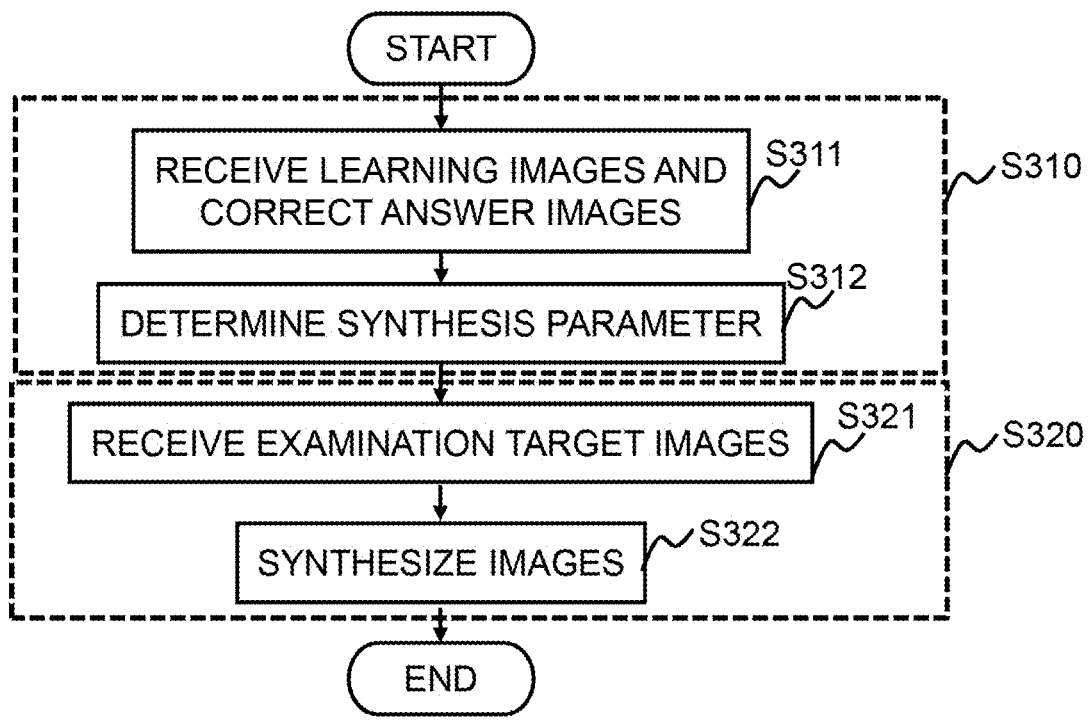

Fig. 5
<LEARNING IMAGES>  
(SELECT 2 IMAGES)
◉ T1 MAP ~411
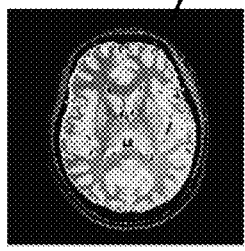
○ T1-EMPHASIZED IMAGE
○ T2 MAP
◉ T2* MAP ~412
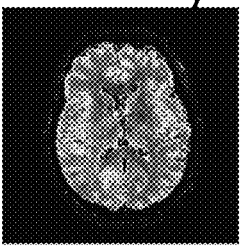
○ T2*-EMPHASIZED IMAGE
○ PD MAP
<CORRECT ANSWER IMAGES>  
(SELECT 1 IMAGE)
○ T2 MAP
◉ T2-EMPHASIZED IMAGE ~420
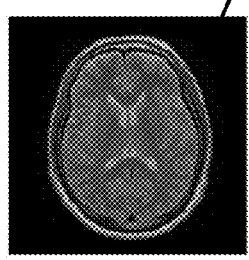
○ T2*-EMPHASIZED IMAGE
○ FLAIR
---
SYNTHESIS PARAMETER VALUE  
CALCULATION RESULT
T1, T2* → T2-EMPHASIZED IMAGE
$A = \{\ ,\ ,\ \}$

Fig. 6
<EXAMINATION TARGET IMAGES>
(LOAD 2 IMAGES)
- ◉ T1 MAP ~431
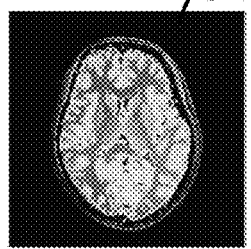
- ○ T1-EMPHASIZED IMAGE
- ○ T2 MAP
- ◉ T2* MAP ~432
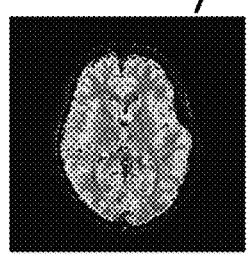
- ○ T2*-EMPHASIZED IMAGE
- ○ PD MAP
<SYNTHESIS PARAMETER VALUE>
- ◉ T1,T2* → T2-EMPHASIZED IMAGE
  A={ , , }
- ○ T1,T2 → T2*-EMPHASIZED IMAGE
  A={ , , }
- ○ T1,T2* → FLAIR
  A={ , , }
- ○ T1,T2* → T2 MAP
  A={ , , }
- ○ T1-EMPHASIZED IMAGE, T2*-EMPHASIZED IMAGE → T2 MAP
  A={ , , }
SYNTHESIZED IMAGE
T2-EMPHASIZED IMAGE
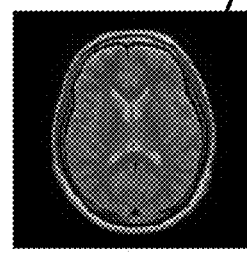
~440

TE1=30 ms    TE2=100 ms

TE=80 ms

MEDICAL IMAGE DIAGNOSIS SUPPORT DEVICE AND MAGNETIC RESONANCE IMAGING APPARATUS

BACKGROUND OF THE INVENTION

Field of the Invention

The present invention relates to a medical image diagnosis support technique using measurement data obtained by a medical image acquisition apparatus.

Background Art

There is a medical image acquisition apparatus that non-invasively obtains an anatomical cross-sectional image of a human body, such as a magnetic resonance imaging (hereinafter, MRI) apparatus, a computed tomography (CT) apparatus, and an ultrasonic diagnostic apparatus. In these apparatuses, an image obtained by calculating the obtained measurement data is displayed as a diagnostic image on a display device attached to the apparatuses or a display device independent from the apparatuses.

For example, an MRI apparatus is a medical image diagnosis support apparatus mainly utilizing a nuclear magnetic resonance phenomenon of protons. The MRI apparatus may non-invasively capture an arbitrary cross section of a subject, and in addition to the morphological information, information on biological functions such as blood flow and metabolic function may be obtained. In the MRI apparatus, in general, physical property values relating to nuclear magnetic resonance of a living tissue, for example, emphasis images in which relative differences such as a longitudinal relaxation time (T1), a transverse relaxation time (T2), and a proton density (PD) are emphasized, are acquired. The degree of emphasis and the physical property values of a target may be changed according to the pulse sequence to be selected and imaging parameters. Specifically, the emphasis image includes a T1-emphasized image in which T1 is emphasized, a T2-emphasized image in which T2 is emphasized, and a T2*-emphasized image in which the transverse relaxation time T2* found under the influence of static magnetic field inhomogeneity is emphasized. In addition, there is also a fluid attenuated IR (FLAIR) image in which a water signal is suppressed by using a sequence called an inversion recovery (hereinafter, IR) method.

In addition, physical property values of a subject (biological tissue) may also be quantitatively calculated by calculation using an image obtained by a specific pulse sequence. For example, the longitudinal relaxation time T1 may be obtained by imaging a plurality of times by using the pulse sequence of the IR method to change inversion time TI. In addition to T1, quantitative images with various physical property values and quantitative values such as T2, T2*, diffusion coefficient, flow rate, magnetic susceptibility, modulus of elasticity, contrast agent concentration, and the like as pixel values may be obtained in the MR apparatus. These quantitative images are also called maps.

In addition, in the CT apparatus, a CT value, and in the ultrasonic diagnostic apparatus, a quantitative image in which the reflectance and the flow rate are visualized is obtained.

Since these emphasis images and quantitative images have different degrees of emphasis of living tissues and physical quantities indicated by pixel values, it is common to capture a plurality of types of images and comprehensively diagnose the images in diagnosis.

Since it takes time to capture a plurality of types of images individually, a method of calculating another type of image from the captured images by calculation is proposed. For example, in U.S. Pat. No. 8,874,189, a method of obtaining quantitative images (maps) of PD, T1, and T2 and synthesizing the values of PD, T1, T2 by calculation using theoretical expressions to generate various emphasis images and further adjust the degree of emphasis to a desired degree by a user's operation has been proposed. In addition, in Japanese Patent No. 6250795, a method of generating images such as a T1-emphasized image and a white matter existence probability map by using the equations calculated by the theoretical expressions or simulation from the quantitative values of PD, T1, T2, and the like has been proposed. Further, Japanese Patent No. 6250795 also discloses a configuration that allows a user to select the type of function (for example, exponential function, logarithmic function, sigmoid function, and the like) used in the equations.

SUMMARY OF THE INVENTION

In the techniques of U.S. Pat. No. 8,874,189 and Japanese Patent No. 6250795, when synthesizing another type of quantitative image or emphasis image from quantitative images, theoretical expressions representing the relationship between pixel values and equations obtained by simulation are used. Therefore, there are no known theoretical expressions or equations are not required in simulation, that is, it is impossible to calculate a quantitative image having another type of quantitative value whose relationship with the quantitative values is unknown and an emphasis image by the techniques of U.S. Pat. No. 8,874,189 and Japanese Patent No. 6250795.

In addition, in Japanese Patent No. 6250795, in order to bring the emphasis degree of an emphasis image (for example, a T1-emphasized image) of a specific characteristic obtained by the synthesis to be close to the degree of emphasis desired by the user, it is possible for the user to manually adjust parameters used for synthesis, or to change the functions of the theoretical expressions and equations to different functions, but generally, it is not possible to manually find such parameters or functions that bring the synthesized image to be close to a quantitative image having another type of quantitative value whose relationship with quantitative values is unknown and an emphasis image or even if it is possible, there is a problem that it takes much time and labor.

For example, from the maps of PD, T1, and T2 obtained by a spin echo sequence, it is not possible to synthesize a T2*-emphasized image by using theoretical expressions. In addition, from the maps of PD, T1, and T2* obtained by a gradient echo sequence, it is not possible to synthesize the T2-emphasized image by using theoretical expressions.

The present invention has been made in view of the above circumstances, and an object thereof is to generate another type of quantitative image and emphasis image from the quantitative images and the emphasis images even if the theoretical expressions or equations representing the relationship between the quantitative images or the emphasis images and another type of quantitative image or emphasis image are not known.

The medical image diagnosis support apparatus of the present invention includes a learning image reception unit that receives two or more learning images and one or more correct answer images, a synthesis parameter determination unit that obtains a synthesis parameter value at which the synthesized pixel value is close to a pixel value of a corresponding pixel of the correct answer image in a case where pixel values of corresponding pixels of the two or more learning images are synthesized by using the synthesis parameter value, an examination target image reception unit that receives an image generated for a first subject and having the same type as the two or more learning images as an examination target image, and an image synthesis execution unit that generates a synthesized image desired by a user by synthesizing pixel values of corresponding pixels of the two or more examination target images by using the synthesis parameter value obtained by the synthesis parameter determination unit. The two or more learning images are two or more types of images generated for the first subject or a second subject different from the first subject. The one or more correct answer images are images generated for the second subject or a third subject different from the first subject and the second subject, a different type of image from the learning images, and the same type of image as the synthesized image.

According to the present invention, it is possible to generate another quantitative image or another emphasis image from pixel values of a quantitative image and an emphasis image by determining a synthesis parameter value by using two or more learning images and correct answer images even if the relationship between the quantitative image and the quantitative image, between the quantitative image and the emphasis image, and between the emphasis image and the emphasis image are not known.

BRIEF DESCRIPTION OF THE DRAWINGS

FIG. 3 is a flowchart showing an operation of the medical image diagnosis support unit according to the first embodiment.

FIG. 5 is an explanatory diagram showing an example of a reception screen for the learning image and the correct answer image in the first embodiment.

FIG. 6 is an explanatory diagram showing an example of a reception screen of the examination target image in the first embodiment.

DETAILED DESCRIPTION OF THE INVENTION

Figure 1:
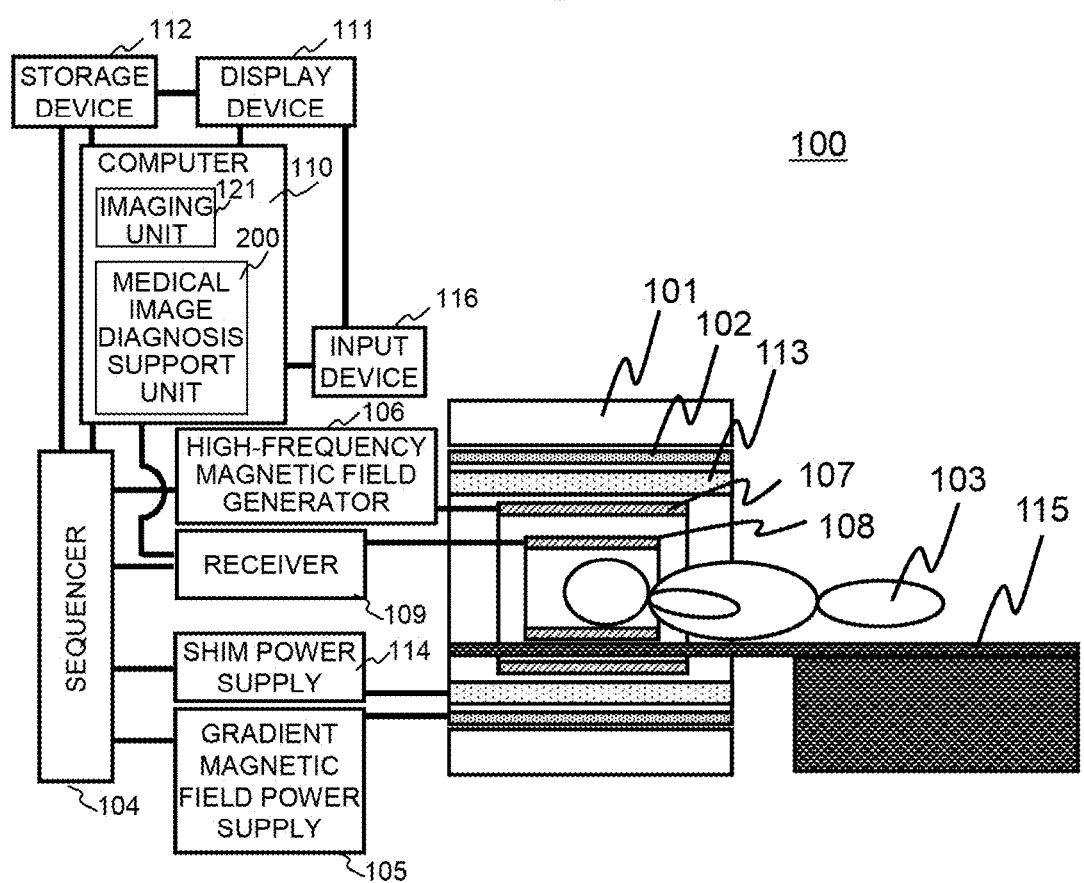
FIG. 1 is a block diagram showing an overall configuration of an MRI apparatus according to a first embodiment.

Embodiments of the present invention will be described with reference to drawings. Thus, the present invention is not limited. In all the drawings for describing the embodiments of the present invention, those having the same function are denoted by the same reference numerals, and repetitive description thereof will be omitted unless otherwise noted.

The inventors focused on synthesizing another type of quantitative image or emphasis image by synthesizing two or more quantitative images or emphasis images by using a suitable synthesis parameter value even if the relationship between a quantitative image or an emphasis image and another type of quantitative image or emphasized image is not known by a theoretical expression or equation and completed the present embodiment.

First Embodiment

Hereinafter, a medical image diagnosis support apparatus according to a first embodiment to which the present invention is applied will be described.

The medical image diagnosis support apparatus of the first embodiment is incorporated in a computer of the MRI apparatus as a medical image diagnosis support unit 200 will be described as an example.

Overall Structure of MRI Apparatus

FIG. 1 shows a typical configuration of an MRI apparatus 100 of the present embodiment. As shown in the drawings, the MRI apparatus 100 includes a magnet 101 for generating a static magnetic field, a gradient magnetic field coil 102 for generating a gradient magnetic field, an RF coil 107 that irradiates a subject (for example, living body) 103 with a high-frequency magnetic field pulse, an RF probe 108 for detecting an echo signal generated from the subject 103, and a bed (table) 115 on which the subject 103 is placed within the static magnetic field space generated by the magnet 101.

Further, the MRI apparatus 100 includes a gradient magnetic field power supply 105 for driving the gradient magnetic field coil 102, a high-frequency magnetic field generator 106 for driving the RF coil 107, a receiver 109 for detecting the echo signal detected by the RF probe 108, and a sequencer 104. The sequencer 104 sends commands to the gradient magnetic field power supply 105 and the high-frequency magnetic field generator 106 to generate gradient magnetic fields and high-frequency magnetic fields, respectively, and also sets a nuclear magnetic resonance frequency serving as a reference for detection on the receiver 109. The respective parts of the above-described MRI apparatus 100 are collectively referred to as measurement units.

In addition to these, the MRI apparatus 100 includes, a computer 110, a display device 111 that displays a processing result in the computer 110, a storage device 112 that holds the processing result, an input device 116 that accepts an instruction from a user. The storage device 112 holds various data necessary for processing in the computer 110.

The computer 110 has at least the functions of an imaging unit 121 and the medical image diagnosis support unit 200. The computer 110 includes a CPU and a memory, and has a configuration in which the functions of the imaging unit 121, the medical image diagnosis support unit 200, and the like are realized by software by CPU loading and executing programs stored in the memory in advance. However, the computer 110 according to the present embodiment is not limited to software that realizes the functions thereof, and all or part of the functions may be realized by hardware such as a custom IC such as an application specific integrated circuit (ASIC) or a programmable IC such as a field programmable gate array (FPGA).

In addition, when it is necessary to adjust the static magnetic field homogeneity, the MRI apparatus 100 may further include a shim coil 113 and a shim power supply 114 for driving the shim coil 113. The shim coil 113 is made up of a plurality of channels and generates an additional magnetic field for correcting the static magnetic field inhomogeneity by the current supplied from the shim power supply 114. The current flowing to each channel constituting the shim coil 113 at the time of adjusting the static magnetic field homogeneity is controlled by the sequencer 104.

In a case where the MRI apparatus 100 having the above configuration performs imaging for a desired imaging region (imaging section) of the subject, the imaging unit 121 of the computer 110 outputs an instruction to the sequencer 104 so that each of the measurement units operates according to a preset program to control the operation of each unit constituting the MRI apparatus 100. When the sequencer 104 sends a command to the gradient magnetic field power supply 105 and the high-frequency magnetic field generator 106, an RF pulse is applied to the subject 103 through the RF coil 107 at the timing and intensity instructed by the computer 110 and a gradient magnetic field pulse is applied by the gradient magnetic field coil 102. A gradient magnetic field is applied to give echo signals position information on slice selection, phase encoding direction, and lead-out direction, the gradient magnetic field pulses in three orthogonal directions are used in combination as appropriate.

An NMR signal (echo signal) in which nuclear magnetization occurs in the tissue of the subject is received by the RF probe 108 and detected (measured) by the receiver 109. The NMR signal is sampled at a predetermined sampling time to be measured as digital data and placed in a measurement space called k space. Measurement of the NMR signal is repeatedly performed until the k space is filled. The measured signal is sent to the computer 110. The computer 110 performs image reconstruction by performing inverse Fourier transform processing on the signal filled in the k space. In the storage device 112, generated images, and as necessary, detected signals themselves, imaging conditions, and the like are stored.

Among the above programs executed by the imaging unit 121 of the computer 110, in particular, the one describing the timing and intensity of the application of the high-frequency magnetic field and the gradient magnetic field, and the timing of receiving the signal are referred to as a pulse sequence. Imaging is performed according to the pulse sequence and the imaging parameters necessary to control the imaging. It is possible to capture an arbitrary imaging cross-section of the subject by controlling the timing and intensity of the high-frequency magnetic field and the gradient magnetic field set in the pulse sequence. The pulse sequence is created in advance and stored in the storage device 112, and imaging parameters are input from the user via the input device 116. The computer 110 controls the user interface such as the input device 116 and the display device 111, accepts input of imaging parameters and the like from the user, and displays the generated image on the display device 111.

Various pulse sequences are known depending on the purpose. For example, a gradient echo (GrE) type of high-speed imaging method is a method of sequentially changing a phase encode gradient magnetic field every repetition time (hereinafter, referred to as TR) of the pulse sequence and measuring the number of NMR signals required to obtain one tomogram or three-dimensional images of a plurality of tomograms. The imaging parameters include a repetition time TR, an echo time TE, a flip angle FA for determining the intensity of the RF pulse, an irradiation phase increment value $\theta$ for the RF pulse, and the like and may be set according to the image to be captured.

By setting the pulse sequence or the imaging parameters in accordance with the quantitative values (values indicating physical property values and characteristics of the subject) to be emphasized and captured, it is possible to capture various types of emphasis images having different degrees of emphasis of physical property values, for example, a T1-emphasized image, a T2-emphasized image, a fluid attenuated inversion recovery (FLAIR) image, a magnetic susceptibility emphasis image, and a diffusion-emphasized image. The physical property values are T1 (longitudinal relaxation time), longitudinal relaxation degree, T2 (transverse relaxation time), PD (proton density), T2* (transverse relaxation time found under the influence of static magnetic field inhomogeneity), degree of transverse relaxation, diffusion coefficient, flow rate, magnetic susceptibility, modulus of elasticity, and contrast agent concentration, and it is possible to calculate a plurality of quantitative values (physical property values or the like) of the tissue of the subject at the position of each pixel of the image by repeating the capturing of the emphasis images a plurality of times while changing the imaging parameters and processing the obtained signals. In this way, it is also possible to generate quantitative images with quantitative values (physical property values and the like) as pixel values, that is, a T1 image with T1 as a pixel value, a T2 image with T2 as a pixel value, and the like.

Configuration of Medical Image Diagnosis Support Unit 200

In addition to the above configuration, the MRI apparatus 100 of the present embodiment includes the medical image diagnosis support unit 200 in the computer 110, which synthesizes another type of emphasis image or quantitative image from emphasis images or quantitative images.

Figure 2:
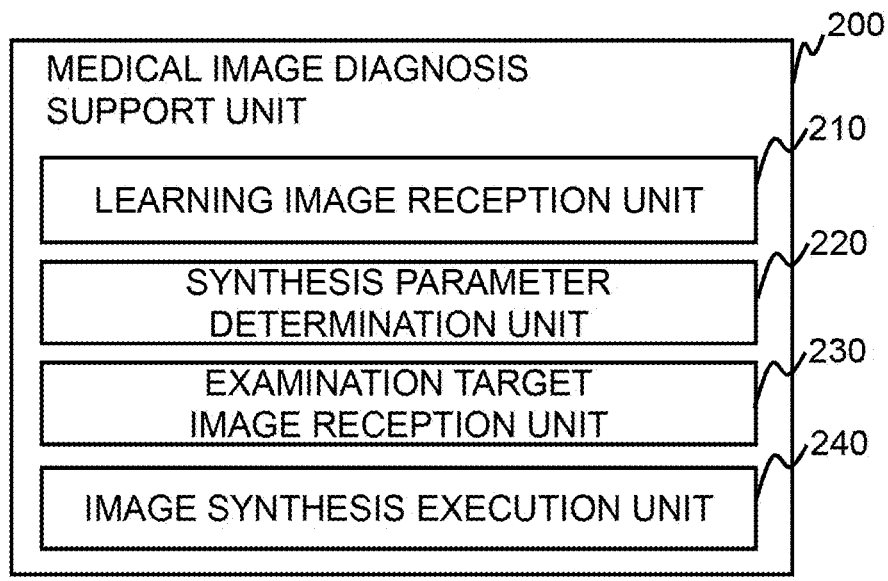
FIG. 2 is a block diagram of a medical image diagnosis support unit according to the first embodiment.

As shown in FIG. 2, the medical image diagnosis support unit 200 of the present embodiment includes a learning image reception unit 210, a synthesis parameter determination unit 220, an examination target image reception unit 230, and an image synthesis execution unit 240.

Operation of Medical Image Diagnosis Support Unit 200

Hereinafter, the outline of the operation of the medical image diagnosis support unit 200 of the present embodiment will be described with reference to the flow of FIG. 3 and FIG. 4.

Before synthesizing an examination target image 430 obtained for the first subject 103 to be examined, the operation of the medical image diagnosis support unit of the present embodiment is divided into pre-examination processing S310 for determining a synthesis parameter value to be used for synthesis and synthesis execution processing S320 for performing combining processing on the examination target image 430.

Figure 4A:
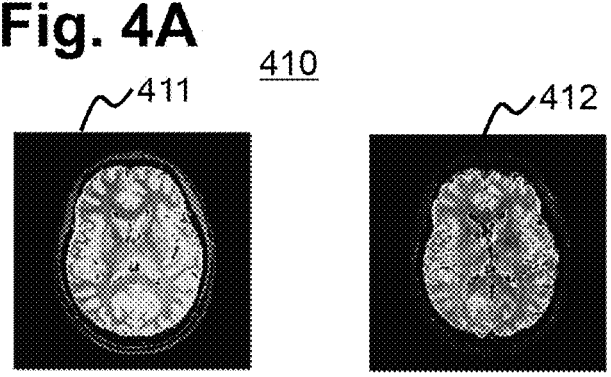
FIG. 4A is an explanatory diagram showing a learning image.
Figure 4B:
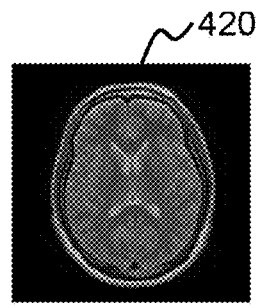
FIG. 4B is an explanatory diagram showing a correct answer image.
Figure 4C:
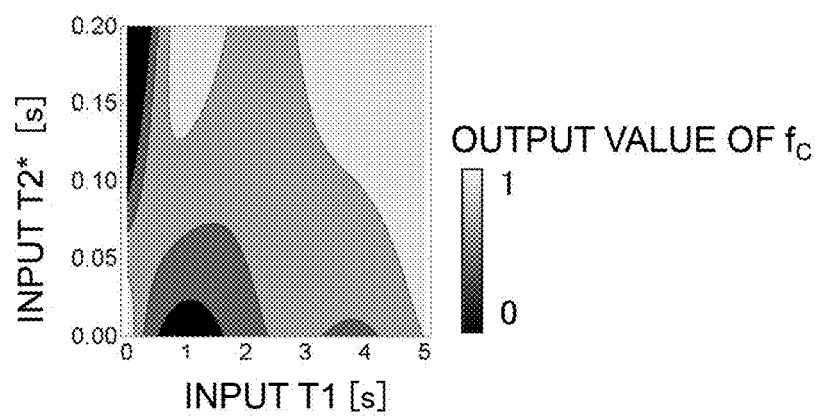
FIG. 4C is an explanatory diagram showing a relationship between pixel values of the learning image or an examination target image and a pixel value $f_c$ of a synthesized image.

First, in the pre-examination processing S310, as shown in FIGS. 4A and 4B, the learning image reception unit 210 receives two or more learning images 410 and one or more correct answer images 420 (step S311). The two or more learning images 410 are two or more images generated for the first subject 103 to be examined or a second subject different from the first subject 103. The correct answer image 420 is an image generated for the second subject or an image generated for a third subject different from the first subject 103 and the second subject, and is a different type of image from the learning image 410. Moreover, the correct answer image 420 is the same type of image as a synthesized image 440 generated for the first subject in the subsequent synthesis execution processing S320.

Next, the synthesis parameter determination unit 220 determines a synthesis parameter value by using the received learning image and the correct answer image (step S312). That is, in a case where the pixel values of the corresponding pixels of two or more learning images 410 are synthesized by a predetermined synthesis method using a synthesis parameter value, the synthesis parameter determination unit 220 obtains a synthesis parameter value at which the synthesized pixel value is close to the pixel value of the corresponding pixel of the correct answer image 420.

Figure 4D:
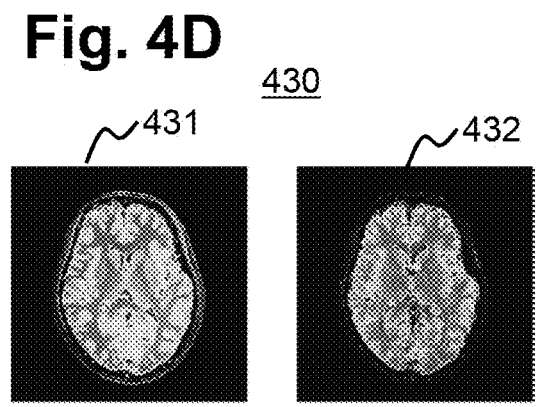
FIG. 4D is an explanatory diagram showing the examination target image.
Figure 4E:
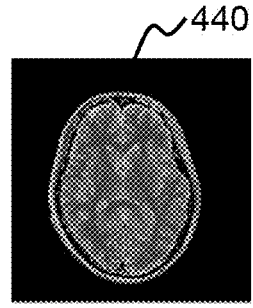
FIG. 4E is an explanatory diagram showing a synthesized image generated by an image synthesis execution unit.

Next, in the synthesis execution processing S320, the examination target image reception unit 230 receives the images generated for the first subject, which are the same type of images as the two or more learning images 410, as the examination target image 430 as shown in FIG. 4D (step S321).

Next, the image synthesis execution unit 240 synthesizes the examination target images 430 received in step S321 by a synthesis method similar to the synthesis method used in step 312 by using the synthesis parameter value determined by the synthesis parameter determination unit 220, and generates and outputs the synthesized image 440 (step S322).

As described above, according to the medical image diagnosis support unit 200 of the present embodiment, it is possible to generate the synthesized image 440 which is a type of quantitative image or an emphasis image whose relationship such as the theoretical expression is not known by synthesizing two or more examination target images (quantitative images or emphasis images) 430 and using an appropriate synthesis parameter value obtained based on the learning image 410 and the correct answer image 420.

As the two or more learning images 410, the correct answer images 420, and the two or more examination target images 430 described above, images captured by the main body of the MRI apparatus of the present embodiment or another MRI apparatus, images generated by magnetic resonance simulation, images generated by calculation using one of the captured images and the simulated images, or any of quantitative images obtained from the captured images and the images generated by the simulation.

As the two or more learning images 410, two or more types of images out of a plurality of types of quantitative images whose pixel values are quantitative values indicating characteristics of the first subject 103 or the second subject to be examined and a plurality of types of emphasis images in which the characteristics are emphasized may be used. One or more correct answer images 420 may be images generated for the second subject, or the third subject different from any of the images of the first subject 103 or the second subject, and different types of quantitative images from the learning image 410 or emphasis images in which characteristics are emphasized may be used. As described above, in the present embodiment, the synthesis parameter value is calculated by using the correct answer image 420 of the subject other than the first subject 103 to be examined.

For example, as the learning image 410 and the correct answer image 420, a quantitative image having a quantitative value of anyone of characteristics out of proton density (PD), longitudinal relaxation time (T1), longitudinal relaxation degree, transverse relaxation time (T2), transverse relaxation time (T2*) found under the influence of static magnetic field inhomogeneity, degree of transverse relaxation, diffusion coefficient, flow rate, magnetic susceptibility, modulus of elasticity, and contrast agent concentration, an emphasis image in which any of the above characteristics is emphasized or a fluid attenuated IR (FLAIR) image in which a water signal is suppressed may be used.

As a specific combination, as the learning image 410, a combination of a T1 image having T1 as a pixel value and a T2* image having T2* as a pixel value may be used, and as the correct answer image 420, a T2 image having T2 as a pixel value or the T2-emphasized image in which T2 is emphasized may be used. In addition, as the learning image 410, a combination of the T1 image having T1 as a pixel value and the T2 image having T2 as a pixel value may be used, and as the correct answer image 420, the T2* image having T2* as a pixel value or the T2*-emphasized image in which T2* is emphasized may be used. In addition, as the learning image 410, a combination of the T1 image having T1 as a pixel value and the T2* image having T2* as a pixel value may be used, and as the correct answer image 420, a FLAIR image may be used.

In addition, as the two or more learning images 410, emphasis images generated from a signal acquired by using a gradient echo sequence or quantitative images calculated from emphasis images may be used, and as the correct answer image 420, the T2 image calculated from a signal acquired by using a spin echo sequence may be used.

Each of the first subject 103, the second subject, and the third subject may be either a human or a phantom.

In addition, it is preferable that the learning image 410 and the correct answer image 420 are images captured or generated at the same position of the same subject or corresponding positions of different subjects, but the learning image 410 and the correct answer image 420 may be images at the same position or corresponding positions adjusted by aligning either one of the learning image 410 and the correct answer image. Thereby, there is an advantage that capturing of the learning image and the correct answer image becomes easy.

Hereinafter, the processing operation of each part of the medical image diagnosis support unit 200 will be described in more detail.

First, for example, the learning image reception unit 210 causes the display device 111 to display a learning image reception screen as shown in FIG. 5 to receive the type of the learning image 410 and specification of a specific image, the type of the correct answer image 420 and specification of a specific image from the user via the input device 116 (step S311). In the learning image reception screen of FIG. 5, any two of the T1 quantitative image (map), the T1-emphasized image, the T2 map, the T2* map, the T2*-emphasized image, and the PD map is selectable as the type of the learning image 410, and any one of the T2 map, the T2-emphasized image, the T2*-emphasized image, and the FLAIR image is selectable as the type of the correct answer image 420. For specific images used in the following processing as the selected type of images, the user specifies images stored in the storage device 112, respectively. In this example, as shown in FIG. 5, the user selects a T1 map 411 and a T2* map 412 as the learning images 410 and selects the T2-emphasized image as the correct answer image 420.

Here, for the learning image 410 and the correct answer image 420, quantitative images calculated by calculation based on emphasis images obtained by capturing images of the second subject different from the first subject to be examined, for example, a healthy volunteer by the imaging unit of the MRI apparatus and emphasis images are used.

Next, the synthesis parameter determination unit 220 obtains a synthesis parameter value for synthesizing pixels using a polynomial having a T1 value and a T2* value as variables (step S312). That is, the synthesis parameter determination unit 220 obtains the parameter A when synthesizing the pixel value of the T1 value and the pixel value of the T2 value of corresponding pixels of the T1 map 411 and the T2 map 422 by using the polynomial expressed by the following Equation (1).

$$f_c(A, T1, T2^*) = \sum_{i,j} a_{ij} T1^i T2^{*j} \ (i + j \le D, 0 \le i, j) \quad (1)$$

In Equation (1), $f_c$ is the synthesized pixel value, T1 and T2* are the T1 value and the T2* value for the pixel, D is the order of the polynomial, and i and j are the order of T1 and T2* in each term of the polynomial.

In addition, in Equation (1), A is a vector that summarizes coefficients $a_{ij}$ of each term of the polynomial and is expressed by the following Equation (2). In the present embodiment, the vector A of the polynomial is the synthesis parameter value.

$$A = \{a_{00}, a_{01}, \ldots a_{ij}, \ldots\}(i+j \le D, 0 \le i, j) \quad (2)$$

Next, the synthesis parameter determination unit 220 obtains a vector A which is a synthesis parameter value by solving the least squares problem expressed by the following Equation (3).

$$A = \underset{A}{\mathrm{argmin}} \sum_{m=1}^{M} |f_c(A, T1_m, T2_m^*) - Iw_m|^2 \quad (3)$$

In Equation (3), M is the total number of pixels included in the learning images 411 and 412, respectively, $T1_m$ and $T2^*_m$ are the T1 and T2 values in a m-th pixel, respectively, and $I_{wm}$ is the pixel value of the correct answer image in the m-th pixel.

That is, the synthesis parameter determination unit 220 determines the vector A which is the synthesis parameter value so that the difference between the synthesized pixel value $f_c$ on the right side of Equation (3) and the pixel value of the corresponding correct answer image 420 becomes small. In other words, the vector A which is the synthesis parameter value is determined such that the synthesized pixel value $f_c$ is close to the pixel value of the corresponding pixel of the correct answer image 420.

Substituting the synthesis parameter value (vector A) obtained by the synthesis parameter determination unit 220 in this manner into Equation (1) yields a function for determining (estimating) the pixel value of the T2-emphasized image from the T1 value and the T2* value as shown in FIG. 4 (c).

Next, the examination target image reception unit 230 causes the display device 111 to display the examination target image reception screen as shown in FIG. 6 to receive the examination target image 430 from the user via the input device 116 (step S321). The image received as the examination target image 430 is the same type of images as the learning images received by the learning image reception unit 210, that is, a T1 map 431 and a T2* map 432. Here, unlike the learning image 410, the examination target image 430 is obtained by imaging the first subject to be examined.

In addition, in a case where there are a plurality types of synthesized images obtained by synthesizing the examination target image 430, the examination target image reception unit 230 also receives a selection of a desired type of synthesized image, that is, a selection of a synthesis parameter value to be used for synthesis. Here, the T2-emphasized image or a FLAIR image may be generated from the T1 map 431 and the T2* map 432, but since the synthesis parameter value is generated by using the T2-emphasized image as the correct answer image in step S312, the synthesis parameter value is selected so that the T2-emphasized image is generated as the type of the synthesized image.

Next, the image synthesis execution unit 240 executes image synthesis using the received T1 map 431 and T2 map 432, the synthesis parameter value (vector A) determined by the synthesis parameter determination unit 220, and Equation (1) used by the synthesis parameter determination unit 220 for synthesis. That is, the image synthesis execution unit 240 generates the synthesized image 440 shown in FIG. 4E by synthesizing the pixel values of the corresponding pixels of the T1 map 431 and the T2 map 432 of the examination target image 430 according to Equation (1) to obtain the synthesized pixel value $f_c$.

As described above, the synthesis parameter value is determined by the synthesis parameter determination unit 220 so as to reduce the difference of the corresponding pixel values between the synthesized image 440 obtained from the T1 map and the T2* map, and the T2-emphasized image. Therefore, the synthesized image 440 is the same type of image as the correct answer image 420, that is, the T2 image.

Next, the image synthesis execution unit 240 displays the synthesized image 440, for example, on the display device 111 and stores the image in the storage device 112. Alternatively, the image synthesis execution unit 240 transmits the image to a display device, a storage device, an image processing device, and the like independent from the MRI apparatus 100. In addition, it is also possible to further perform image processing on the synthesized image 440 by an image processing program or the like independent from the medical image diagnosis support unit 200 to display the obtained image on the display device 111 or the like.

As described above, even in a case where the relationship between the pixel values of the image to be input and the image to be synthesized is not known, the medical image diagnosis support apparatus (MRI apparatus) of the present embodiment may obtain a desired type of synthesized image by the user with a simple operation.

In particular, in a case where an emphasis image is set as a correct answer image, since an image having the same degree of emphasis as that of the emphasis image widely acquired by imaging in the related art may be obtained by synthesis, there is an advantage that the examination time may be shortened as compared with the examination time in the related art. In addition, in a case where quantitative images are set as correct answer images, in general, quantitative images that take time for capturing and computation may be obtained in a short time by synthesis, quantitative images may be obtained almost simultaneously with other types of quantitative images, and there is an advantage that quantitative images may be obtained without prolonging the examination time.

In particular, in a case where quantitative images such as the T1 map and the T2* map obtained by using the gradient echo sequence, emphasis images such as the T1-emphasized image, the T2*-emphasized image or the like are set as learning images, and the T2 map is obtained by using the spin echo sequence, since another emphasis image may be synthesized from the synthesized T2 map by using a known method, there is an advantage that the effect of shortening the examination time is increased.

Various sequences may be used as the gradient echo sequence, but it is preferable to capture images under a plurality of imaging conditions having different combinations of flip angle, RF phase increment value, TR, and TE by using the RF-spoiled steady state gradient echo (RSSG) sequence to use the obtained emphasis image or the PD, T1, and T2* images calculated from the emphasis images as learning images. With the RSSG sequence, a three-dimensional image may be acquired at a high rate, and therefore there is an advantage that the three-dimensional T2 map may be acquired at the same time in addition to the three-dimensional PD, T1, and T2* map which is possible with the RSSG sequence in the related art, by configuring the medical image diagnosis support unit 200 so as to be able to acquire the T2 image.

Modification Example 1

As shown in the flow of FIG. 3, the pre-examination processing S310 for determining the synthesis parameter value is performed every time the synthesis processing S320 is performed on the image to be examined, but the pre-examination processing S310 may be also performed before imaging the subject 103 to be examined before the MRI apparatus 100 is shipped or after the MRI apparatus is installed at a clinical site after shipment.

That is, if the combination of the type of the examination target image 430 and the type of the correct answer image 420 is the same, the pre-inspection processing S310 for determining the synthesis parameter value may be performed once before the synthesis execution processing S320 to obtain the synthesis parameter value (vector A). Therefore, it is possible to obtain the synthesis parameter value beforehand and to store the value in the storage device 112 for each combination of the type of the examination target image 430 and the type of the correct answer image 420 that may be received by the learning image reception unit 210 before the MRI apparatus 100 including the medical image diagnosis support unit 200 is shipped. In the synthesis execution processing S320, when the examination target image reception unit 230 receives an examination target image, for example, as shown in the reception screen in FIG. 6, the synthesis parameter value corresponding to the combination of the types of the examination target image to be synthesized this time and a synthesized image is selected from among the synthesis parameter values previously determined.

Modification Example 2

Here, an example of generating the learning image 410 and the correct answer image 420 by simulation will be described. As the simulation, for example, a known method of calculating the signal value of the emphasis image by simulation may be used from a combination of quantitative values such as T1, T2, proton density, and the like. The T1 map, the T2 map, the proton density image, and the like are obtained by aligning the general T1 value, T2 value, proton density, and the like of the living tissue, respectively and an emphasis image is created by obtaining the pixel value (luminance) of the emphasis image by simulation from the T1 value, the T2 value, and the proton density for each pixel. The T1 map and the T2 map may be used as the learning image 410, and the emphasis image obtained by the simulation may be used as the correct answer image 420.

Modification Example 3

The learning image 410, the correct answer image 420, and the examination target image 430 are not limited to a two-dimensional image, but may be data formats such as a one-dimensional image and a three-dimensional image. In addition, the set of the learning image and the correct answer image is not limited to one, but may be plural. In that case, the synthesis parameter value may be determined by Equation (3) by assigning a serial number to all the sets of pixels to m. For example, it is possible to reduce subject dependency in determining a synthesis parameter by using a plurality of sets of learning images and correct answer images acquired by each of a plurality of subjects.

Modification Example 4

The synthesis means 210 has been described by exemplifying the case where the pixel value of a synthesized image is obtained by using the polynomial of the pixel value, but various conversion functions may be similarly used in addition to the polynomial. For example, a polynomial, a reciprocal, an exponential function, a logarithmic function, a sigmoid function, a trigonometric function, an absolute value, a step function, or a combination thereof may be used. The parameter of each function is the synthesis parameter value. Due to the range and distribution of the pixel values of the correct answer image, there is an advantage that the difference between the synthesized image and the correct answer image may be reduced as compared with the case of using the polynomial.

The learning image reception unit 210 may be configured to receive three or more types of emphasis images or quantitative images as the learning images 410. In that case, the function to be used for synthesis is a function of a polynomial or the like with pixel values of corresponding pixels of three or more images as input, and the parameter of the function is the synthesis parameter value. In addition, the examination target image reception unit 230 receives three or more types of examination target images 430 that are the same as the learning image 410 with respect to a subject to be examined. For the subject to be examined, since a synthesized image is obtained by using more images than two types of images, there is an advantage that the image quality is improved.

Modification Example 5

In the above description, the synthesis parameter determination unit 220 determines the synthesis parameter value by using the least squares method such that the difference between the synthesized pixel value in the case where the pixel values of the learning images 410 are synthesized by using an equation and the pixel value of the correct answer image 420 is reduced, but there are various methods for determining the synthesis parameter value for reducing the difference. For example, the least squares method with constraint terms on the magnitude of the value of the synthesis parameter, the method of maximizing the correlation coefficient of the pixel values of the synthesized image and the correct answer image, and the like may be adopted. In addition, a known method called machine learning or deep learning may also be adopted as a synthesis parameter determination method for bringing an image obtained by synthesizing learning images to be close to a correct answer image.

Second Embodiment

Next, a second embodiment of the present invention will be described. The second embodiment has basically the same configuration as the medical image diagnosis support apparatus of the first embodiment, but unlike the first embodiment, the second embodiment has a function of adjusting a synthesized image to be output with a predetermined imaging parameter (adjustment parameter) other than the pixel values of two or more examination target images. As a result, it is possible to generate a synthesized image having a desired adjustment parameter value from two or more examination target images.

Since the medical image diagnosis support unit 200 of the second embodiment has the same configuration as that of the first embodiment, different configurations and operations will be described below with reference to FIGS. 7, 8, 9A and 9B.

Figure 7:
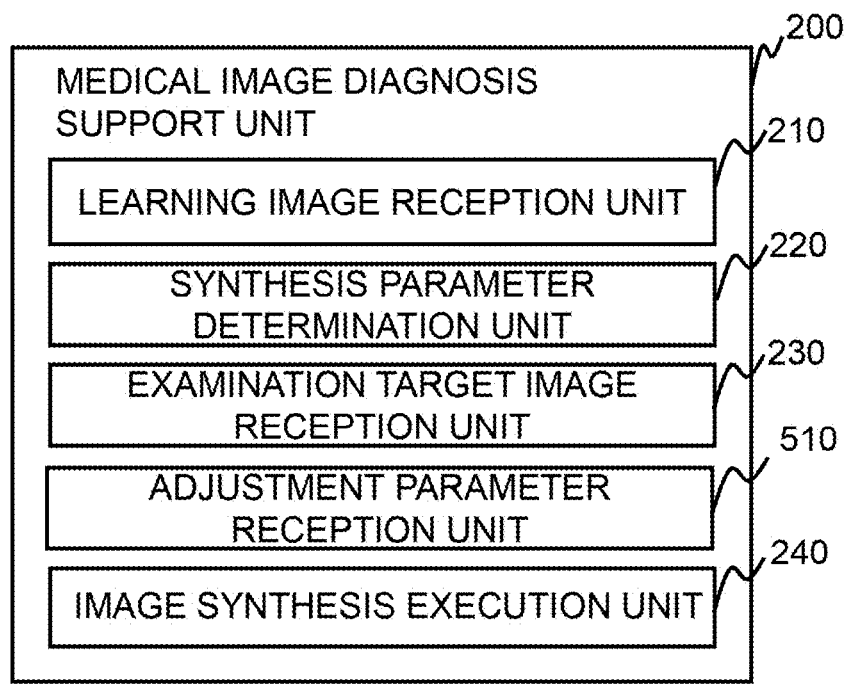
FIG. 7 is a block diagram of a medical image diagnosis support unit according to a second embodiment.

Configuration of Medical Image Diagnosis Supporting Unit 200 of Second Embodiment In addition to the configuration of the first embodiment, the medical image diagnosis support unit 200 further includes an adjustment parameter reception unit 510 that receives an adjustment parameter value for adjusting a synthesized image as shown in FIG. 7. The adjustment parameter value is a value of a predetermined imaging parameter that affects when capturing or generating a quantitative image or an emphasis image of the same type as the correct answer image. An example of the predetermined imaging parameter may be one of an echo time (TE), a repetition time, an inversion time, a diffusion time, and a flip angle.

Figure 9A:
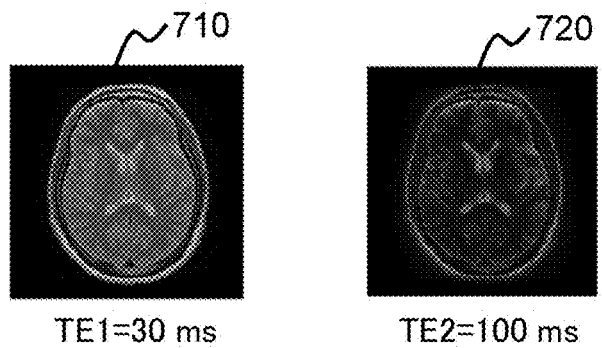
FIG. 9A is an explanatory diagram showing a first correct answer image and a second correct answer image.

The learning image reception unit 210 receives two or more learning images and correct answer images, but in the second embodiment, the learning image reception unit 210 receives two or more images 710 and 720 (for example, TE=30 ms and 100 ms) of the same type of quantitative image or emphasis image captured or generated under different conditions of the predetermined imaging parameter (here, TE) as correct answer images as shown in FIG. 9A.

In a case where pixel values of corresponding pixels of two or more learning images (images 410 and 411 in FIG. 4) received by the learning image reception unit 210 are synthesized by using values (TE=30 ms and 100 ms) of the imaging parameter (TE), the synthesis parameter determination unit 220 obtains a synthesis parameter value at which the synthesized pixel values are close to pixel values of corresponding pixels of two or more correct answer images 710 and 720 in FIG. 9A. Specifically, in a case where pixel values of corresponding pixels of two or more learning images 410 and 411 are synthesized by using a predetermined equation (for example, Expression (4) described later) having the pixel values of the two or more learning images 410 and 411 and the value of the imaging parameter (TE) as variables, the synthesis parameter determination unit 220 obtains a synthesis parameter value at which the synthesized pixel values are close to the pixel values of corresponding pixels of two or more correct answer images 710 and 720, respectively.

The image synthesis execution unit 240 generates a synthesized image 730 by synthesizing the pixel values of corresponding pixels of two or more examination target images (images 431 and 432 in FIG. 4D) received by the examination target image reception unit 230 with the synthesis parameter value obtained by the synthesis parameter determination unit 220 and the imaging parameter value (for example, TE=80 ms) received by the adjustment parameter reception unit 510 by using the above-described predetermined equation.

Thereby, it is possible to generate the synthesized image 730 which is the same type of quantitative image or emphasis image as the correct answer images 710 and 720 from the examination target images without imaging under the condition of the imaging parameter value (TE=80 ms) received by the adjustment parameter reception unit 510.

Operation of Medical Image Diagnosis Support Unit 200 of Second Embodiment

The operation of the medical image diagnosis support unit 200 according to the second embodiment will be specifically described with reference to FIG. 8.

First, the learning image reception unit 210 receives a T1 map 411 and a T2*map 412 as the learning image 410. Further, the learning image reception unit 210 receives the first correct answer image 710 which is a predetermined type of quantitative image or emphasis image (here, T2-emphasized image) different from the learning image 410 and has a first adjustment parameter value (imaging parameter value) (TE1=30 ms), and the second correct answer image 720 having a second adjustment parameter value (TE2=100 ms) different from the first adjustment parameter value (step S311).

As a method of associating the correct answer image with the adjustment parameter value, for example, the medical image diagnostic support unit 200 may be configured so that the first and second adjustment parameter values are determined in advance and a correct answer image matching the value may be received or may be configured so that the user inputs the first adjustment parameter value and the second adjustment parameter value in accordance with the conditions for capturing the first and second correct answer images 710 and 720 and the like via the user interface.

For a synthesized image obtained by synthesizing the learning images 411 and 412 by using the synthesis parameter value according to the following Equations (4) to (6), the synthesis parameter determination unit 220 determines a synthesis parameter value (vector A) so that the difference from the first correct answer image 710 becomes small when TE is the first value TE1 (here, 30 ms) and the difference from the second correct answer image 720 becomes small when the TE is the second value TE2 (here, 100 ms) (step S312).

$$f_c(A, T1, T2^*, TE) = \sum_{i,j,k} a_{ijk} T1^i T2^{*j} TE^k \quad (i+j+k \leq D, 0 \leq i, j) \quad (4)$$

$$A = \{a_{000}, a_{001}, \ldots a_{ijk}, \ldots \} \quad (i+j+k \leq D, 0 \leq i, j, k) \quad (5)$$

$$A = \underset{A}{\mathrm{argmin}} \sum_{m=1}^{M} \sum_{n=1}^{N} |f_c(A, T1_m, T2^*_m, TE_n) - Iw_{nm}|^2 \quad (6)$$

In Equation (4), $f_c$ is the synthesized pixel value, T1 and T2* are the corresponding pixel values of the learning images 411 and 412, D is the degree of the polynomial, and i, j, and k are the values of T1, T2*, and TE in each term of the polynomial, respectively. In Equation (5), A is a vector that summarizes the coefficients $a_{ijk}$ of each term of the polynomial. In Equation (6), M is the total number of pixels included in the image, N is the number of adjustment parameter values (here, N is 2), $T1_m$ and $T2^*_m$ are T1 and T2 values in the m-th pixel, and $I_{wnm}$ is the pixel value of the correct answer image in the m-th pixel.

Next, the examination target image reception unit 230 receives the examination target image 430 (431 and 432) as in the first embodiment (step S321).

Next, the adjustment parameter reception unit 510 receives the adjustment parameter value (here, TE=80 ms) to be used in image synthesis via the input device 116 (step S610). A method for the adjustment parameter reception unit 510 to receive the adjustment parameter value may include, for example, a method in which the user inputs numerical values using a keyboard or a method in which the user selects one from the options displayed on the display device 111 by the adjustment parameter reception unit 510 by using a mouse.

Figure 9B:
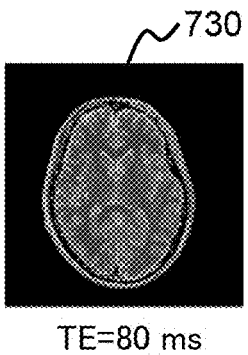
FIG. 9B is an explanatory diagram showing a synthesized image generated by an image synthesis execution unit of the second embodiment.

Next, the image synthesis execution unit 240 calculates the synthesized pixel value for each pixel of the examination target image 430 to generate the synthesized image 730 shown in FIG. 9B by using the pixel values of the T1 map 431 and the T2 map 432 which are the received examination target images 430, the synthesis parameter value (vector A) determined by the synthesis parameter determination unit 220, the adjustment parameter value (TE=80 ms) received in step S610, and Equations (4) and (5).

As a result, it is possible to generate an image having a degree of emphasis close to that of the T2-emphasized image captured with the adjustment parameter value (TE=80 ms) received from the user in accordance with the values of the first adjustment parameter value (TE=30 ms), the second adjustment parameter value (TE=100 ms), and the adjustment parameter value (TE=80 ms) received from the user. As a result, it is possible to obtain a synthesized image in which the user has adjusted the degree of emphasis as desired.

The first correct answer image 710 and the second correct answer image 720 of the present embodiment may be images having different imaging parameters (adjustment parameters) other than TE. For example, FLAIR images having different inversion times TI may be used as the first and second correct answer images 710 and 720, the adjustment parameter reception unit 510 may receive the value of the TI desired by the user, and the image synthesis execution unit 240 may generate a synthesized image by using the received TI.

In addition, the second embodiment is not limited to images captured or generated by the MRI apparatus, and it is possible to use any medical image as the correct answer images 710 and 720 to set corresponding adjustment parameter values to predetermined values such as 0 and 1, and it is also possible for the adjustment parameter reception unit to receive any value between 0 and 1 and the image synthesis execution unit 240 to generate a synthesized image by using the received value. Thereby, it is possible to obtain an image having an intermediate degree of emphasis of any two correct answer images.

The learning image reception unit 210 of the present embodiment receives the first correct answer image and the second answer correct answer image, but three or more correct answer images corresponding to three or more values of adjustment parameters may be received. Since the number of the values of the adjustment parameters corresponding to the correct answer images increases, there is an advantage that the relationship between the adjustment parameter and the degree of emphasis becomes accurate.

As the learning images and the correct answer images in the second embodiment, various medical images may be used as in the first embodiment, but it is preferable that the learning images are emphasis images captured by using a GrE sequence or quantitative images measured by using the GrE sequence and the correct answer images are emphasis images captured by using an SE sequence. Since imaging is performed with the GrE sequence having shorter imaging time as compared with the SE sequence and an image obtained by the SE sequence may be obtained by synthesis, the examination time may be greatly shortened.

Third Embodiment

Figure 10:
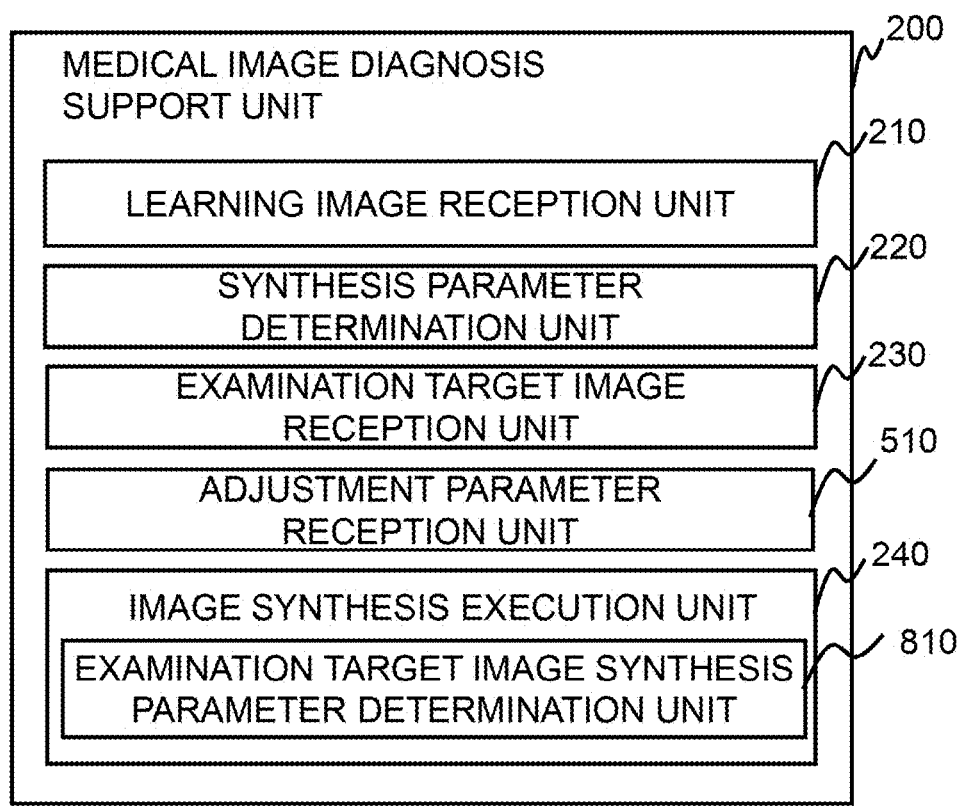
FIG. 10 is a block diagram of a medical image diagnosis support unit according to a third embodiment.
Figure 11:
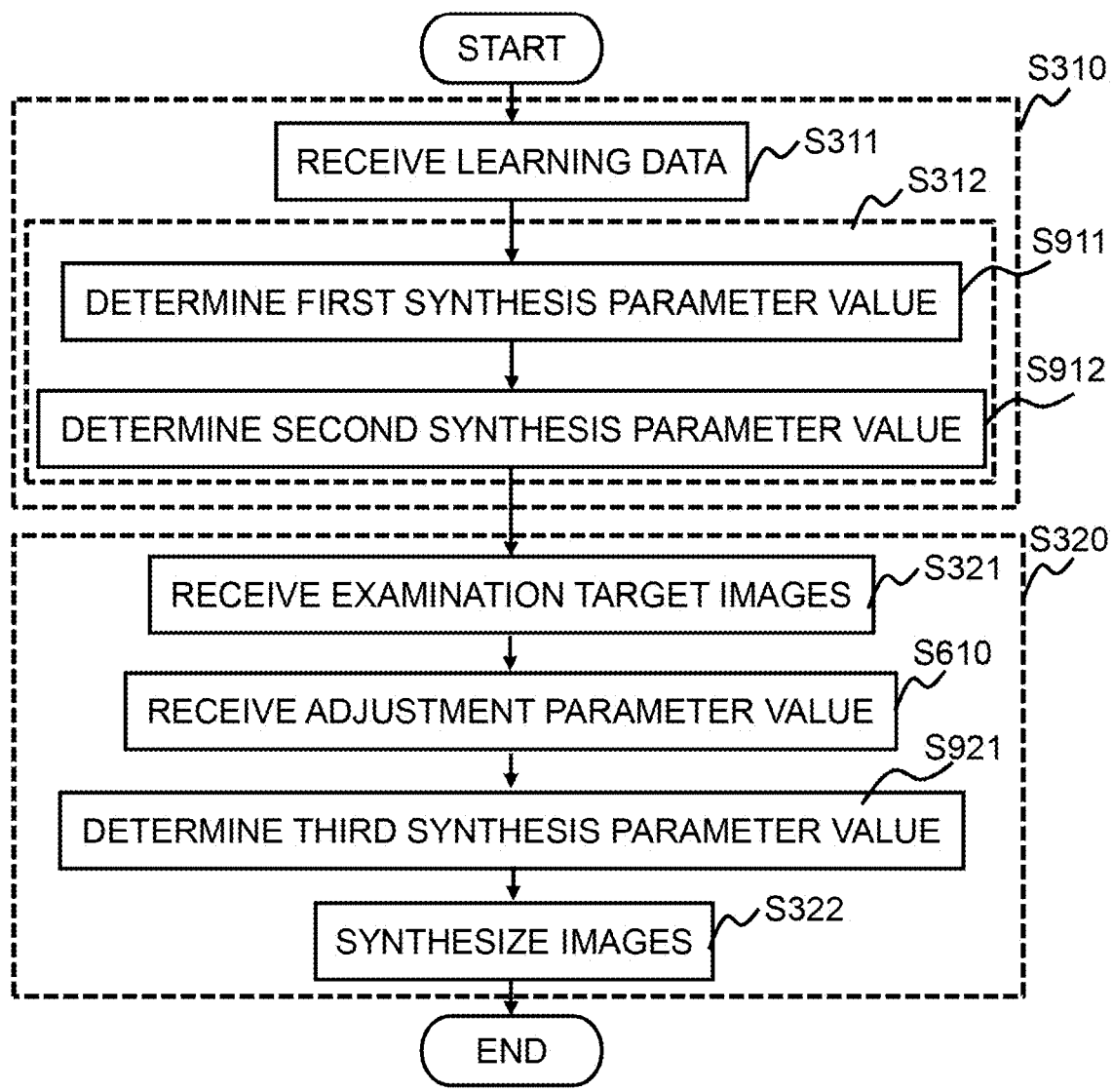
FIG. 11 is a flowchart showing an operation of the medical image diagnosis support unit of the third embodiment.

Next, a third embodiment of the present invention will be described with reference to FIGS. 10 and 11. The third embodiment basically has the same configuration as the medical image diagnosis support unit of the second embodiment, but differs from the second embodiment in the following points.

That is, the synthesis parameter determination unit 220 obtains the synthesized pixel values of the corresponding pixels of two or more learning images 411 and 412, a first synthesis parameter value close to the pixel value of the first correct answer image 710, and a second synthesis parameter value close to the pixel value of the second correct answer image 720.

Figure 8:
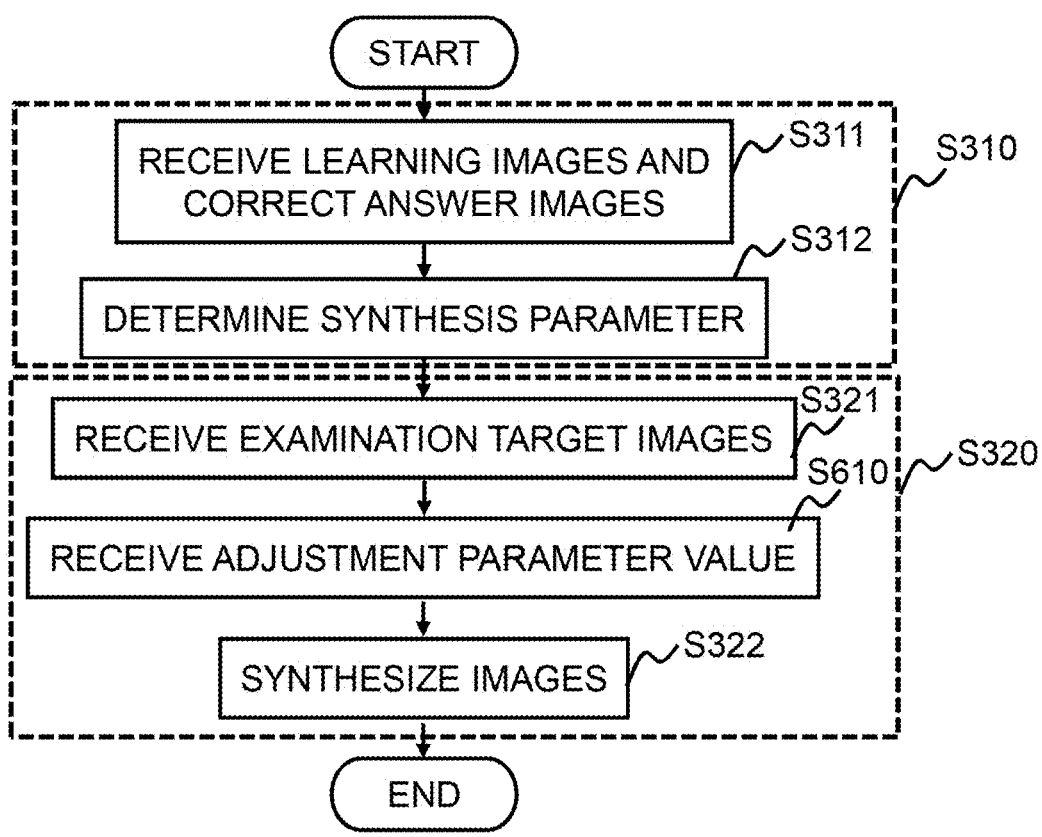
FIG. 8 is a flowchart showing an operation of the medical image diagnosis support unit of the second embodiment.

In addition, as shown in FIG. 8, the image synthesis execution unit 240 includes an examination target image synthesis parameter determination unit 810. The examination target image synthesis parameter determination unit 810 generates a third synthesis parameter value by weighting the first synthesis parameter value and the second synthesis parameter value according to the ratio between each of the first imaging parameter value and the second imaging parameter value and the imaging parameter value received by the adjustment parameter reception unit 510 and then synthesizing the first synthesis parameter value and the second synthesis parameter value. Using the third synthesis parameter value, the image synthesis execution unit 240 synthesizes the pixel values of the corresponding pixels of two or more examination target images 431 and 432 and generates a synthesized image.

Hereinafter, the operation of each part of the medical image diagnosis support unit 200 of the third embodiment will be specifically described. Parts different from those of the second embodiment will mainly be described.

As in the second embodiment, the learning image reception unit 210 receives the T1 map 411 and the T2 map 412 as the learning images 410. Next, the first correct answer image 710 having the first adjustment parameter value (for example, TE=30 ms) and the second correct answer image 720 having the second adjustment parameter value (TE=100 ms) are received (step S311).

Next, similarly to the synthesis parameter determination unit 220 described in the first embodiment, the synthesis parameter determination unit 220 according to the present embodiment obtains a first synthesis parameter value A (set to be A1) by using the above-described Equation (3) so that the difference between the synthesized pixel value of the corresponding pixels of the learning images 411 and 412 and the pixel value of the corresponding pixel of the first correct answer image 710 becomes small (step S911). Similarly, a second synthetic parameter value A (set to be A2) is obtained by using Equation (3) so that the difference between the synthesized pixel value of the corresponding pixels of the learning images 411 and 412 and the pixel value of the corresponding pixel of the second correct answer image 720 becomes small (step S912).

Next, the examination target image reception unit 230 receives the examination target images 431 and 432 as in the second embodiment (step S321).

Next, the adjustment parameter reception unit 510 receives the adjustment parameter value (here, TE=80 ms) to be used in image synthesis via the input device 116 (step S610).

The examination target image synthesis parameter determination unit 810 calculates the third synthesis parameter value for obtaining a synthesis result according to the adjustment parameter value (TE=80 ms) received by the adjustment parameter reception unit 510 (step S921).

Specifically, the examination target image synthesis parameter determination unit 810 calculates the third synthesis parameter value by using the following Equation (7) from the adjustment parameter value, the first and second adjustment parameter values (here, TE1=30 ms and TE2=100 ms) corresponding to the first and second correct answer images 710 and 720, and the first synthesis parameter value A1 and the second synthesis parameter value A2.

$$A3 = p \cdot A1 + (1-p) \cdot A2 \quad (7)$$

In Equation (7), p is a value determined according to the adjustment parameter value TE received by the adjustment parameter reception unit 510 and TE1 and TE2 of the first and second adjustment parameter values and is expressed by the following Equation (8).

$$p = \frac{TE2 - TE}{TE2 - TE1} \quad (8)$$

By using p in Equation (8), a synthetic parameter value A3 of Equation (7) is a value obtained by linearly interpolating the synthesis parameter value A1 and the synthesis parameter value A2 in accordance with the adjustment parameter value TE received by the adjustment parameter reception unit 510 and the values of TE1 and TE2 of the first and second adjustment parameter values.

Next, the image synthesis execution unit 240 generates a synthesized image by obtaining the pixel value of the synthesized image by using the pixel values of the examination target images 431 and 432 received in step S321, the third synthesis parameter value determined in step S921, and Equation (1).

Thereby, it is possible to obtain a synthesized image with a high degree of emphasis set by the user based on the adjustment parameter value (TE=80 ms) received by the adjustment parameter reception unit 510.

In the third embodiment, unlike the second embodiment, the adjustment parameter values received by the adjustment parameter reception unit 510 are not processed by the synthesis parameter determination unit 220 and the image synthesis execution unit 240 but are used only in the examination target image synthesis parameter determination unit 810. As a result, there is an advantage that the calculation time of image synthesis may be shortened.

What is claimed is:

1. A medical image diagnosis support apparatus comprising:
   a computer configured to:
      receive two or more learning images and one or more correct answer images;
      obtain a synthesis parameter value by reducing difference between synthesized pixel values and pixel values of a corresponding pixel of the one or more correct answer images when pixel values of corresponding pixels of the two or more learning images are synthesized as the synthesized pixel values by using a conversion function of at least the pixel values of the corresponding pixels of the two or more learning images and the synthesis parameter value;
      receive two or more examination target images generated for a first subject, and having the same type as the two or more learning images; and
      generate a synthesized image for a user by synthesizing pixel values of corresponding pixels of the two or more examination target images as the pixel values of corresponding pixels of the synthesized image by using at least the conversion function and the synthesis parameter value where the pixel values of the corresponding pixels of the two or more examination target images are used instead of the pixel values of the two or more learning images in the conversion function,
   wherein the two or more learning images are two or more types of images generated for the first subject, or a second subject different from the first subject, and
   the one or more correct answer images are images generated for the second subject, or a third subject different from the first subject and the second subject, and having a different type from the learning images, and having the same type as the synthesized image for the user.

2. The medical image diagnosis support apparatus according to claim 1,
   wherein the two or more learning images are two or more types of images out of a plurality of types of quantitative images whose pixel values are quantitative values indicating characteristics of the first subject or the second subject, and a plurality of types of emphasis images in which the characteristics are emphasized, and
   the one or more correct answer images are quantitative images or emphasis images in which characteristics are emphasized that are different from the learning images.

3. The medical image diagnosis support apparatus according to claim 2,
   wherein the two or more learning images, the one or more correct answer images, and the two or more examination target images are any of images captured by a magnetic resonance imaging apparatus, images generated by magnetic resonance imaging simulation, images generated by calculation using one of the captured images and the images generated by the simulation, and images having quantitative values obtained from the captured images and the images generated by the simulation.

4. The medical image diagnosis support apparatus according to claim 3,
   wherein the learning images are, an emphasis image generated from a signal acquired by using a gradient echo sequence, or a quantified image calculated from the emphasis image, and the correct answer images are a T2 image calculated from a signal acquired by using a spin echo sequence.

5. The medical image diagnosis support apparatus according to claim 3, wherein the computer is further configured to:
receive an adjustment parameter value for adjusting the synthesized image, which is a value of an imaging parameter that affects the images when capturing or generating the same type of quantitative image or emphasis image as the correct answer images,
wherein the receiving one or more correct answer images includes receiving two or more correct answer images captured or generated under conditions having different values of the imaging parameter,
obtain the synthesis parameter value by reducing difference between the synthesized pixel values and pixel values of corresponding pixels of the two or more correct answer images when the pixel values of corresponding pixels of the two or more learning images are synthesized as the synthesized pixel values by using the values of the imaging parameter as values of the adjustment parameter respectively, and
generate the synthesized image by synthesizing pixel values of corresponding pixels of the two or more examination target images by using the synthesis parameter value and the adjustment parameter value received.

6. The medical image diagnosis support apparatus according to claim 5,
wherein the computer is configured to:
when pixel values of corresponding pixels of the two or more learning images are synthesized by using a predetermined equation having pixel values of the two or more learning images and the value of the imaging parameter as variables, obtain the synthesis parameter value by reducing difference between the synthesized pixel values and the pixel values of corresponding pixels of the two or more correct answer images by using the values of the imaging parameter as values of the adjustment parameter, respectively and
generate the synthesized image by synthesizing pixel values of corresponding pixels of the two or more examination target images by using the synthesis parameter value and an imaging parameter value received by the computer according to the predetermined equation.

7. The medical image diagnosis support apparatus according to claim 5,
wherein the computer is further configured to:
receive a first correct answer image captured or generated with a first imaging parameter value for the value of the imaging parameter and a second correct answer image captured or generated with a second imaging parameter value, as the correct answer image,
obtain a first synthesis parameter value by reducing difference between the synthesized pixel value of the corresponding pixels of the two or more learning images and a pixel value of the first correct answer image and a second synthesis parameter value by reducing difference between the synthesized pixel value and a pixel value of the second correct answer image, as the synthesis parameter value, and
generate a third synthesis parameter value by weighting the first synthesis parameter value and the second synthesis parameter value according to a ratio between each of the first imaging parameter value and the second imaging parameter value and the imaging parameter value received by the computer, and
then synthesize the first synthesis parameter value and the second synthesis parameter value and generate a synthesized image by synthesizing pixel values of corresponding pixels of the two or more examination target images by using the third synthesis parameter value.

8. The medical image diagnosis support apparatus according to claim 5,
wherein the predetermined imaging parameter is one of an echo time (TE), a repetition time, an inversion time, a diffusion time, or a flip angle.

9. The medical image diagnosis support apparatus according to claim 1,
wherein the learning images and the correct answer images are a quantitative image having a quantitative value of any one of characteristics out of a proton density (PD), a longitudinal relaxation time (T1), degree of longitudinal relaxation, a transverse relaxation time (T2), a transverse relaxation time (T2*) found under an influence of static magnetic field inhomogeneity, degree of transverse relaxation, a diffusion coefficient, flow rate, magnetic susceptibility, modulus of elasticity, and contrast agent concentration, or an emphasis image in which any of the characteristics is emphasized, or a fluid attenuated IR (FLAIR) image in which a water signal is suppressed.

10. The medical image diagnosis support apparatus according to claim 9,
wherein the learning images are a T1 image having T1 as a pixel value and a T2* image having T2* as a pixel value, and the correct answer images are a T2 image having T2 as a pixel value or a T2-emphasized image in which T2 is emphasized.

11. The medical image diagnosis support apparatus according to claim 9,
wherein the learning images are a T1 image having T1 as a pixel value and a T2 image having T2 as a pixel value, and the correct answer images are a T2* image having T2* as a pixel value or a T2*-emphasized image in which T2* is emphasized.

12. The medical image diagnosis support apparatus according to claim 9,
wherein the learning images are a T1 image having T1 as a pixel value and a T2* image having T2* as a pixel value, and the correct answer images are a FLAIR image.

13. The medical image diagnosis support apparatus according to claim 1,
wherein the computer is configured to synthesize the pixel values by conversion processing using a polynomial, an inverse number, an exponential function, a logarithmic function, a sigmoid function, a trigonometric function, an absolute value, a step function, or a combination thereof, and
the synthesis parameter value is a parameter value of the conversion processing.

14. The medical image diagnosis support apparatus according to claim 1,
wherein the learning images and the correct answer images are images captured or generated at the same position of the same subject or corresponding positions of different subjects or images at the same position or corresponding positions adjusted by aligning either one of the learning images and the correct answer images.

15. A magnetic resonance imaging apparatus comprising:
the medical image diagnosis support apparatus according to claim 1.

* * * * *